Feb. 1, 1966 M. L. WHISLER Plant Pat. 2,593
ROSE PLANT
Filed Nov. 17, 1964
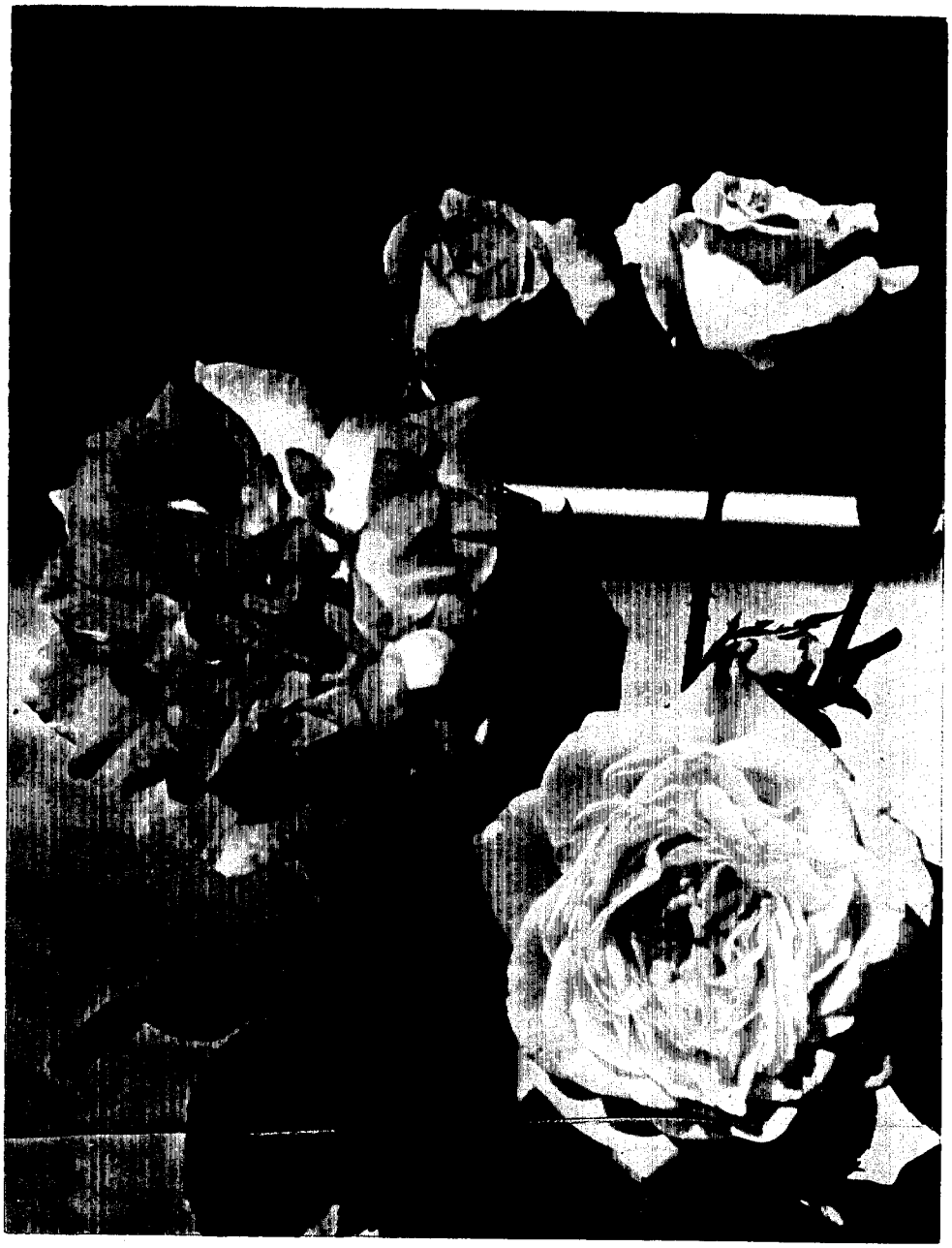
Inventor.
Milton L. Whisler
By: Robb & Robb
Attorneys.

United States Patent Office

Plant Pat. 2,593
Patented Feb. 1, 1966

2,593
ROSE PLANT

Milton L. Whisler, Shafter, Calif., assignor to Germain's, Inc., Los Angeles, Calif., a corporation of California Filed Nov. 17, 1964, Ser. No. 411,952
1 Claim. (Cl. Plt.—27)

The present invention relates to a new and distinct variety of rose plant of the floribunda class, which was originated by me by crossing the variety known as "Easter Parade" (Plant Patent No. 1,200) with the variety "Herrenhausen" (unpatented).

As the result of this breeding, I have succeeded in producing a new and improved rose variety which is distinctively different from its parents, as well as from all other varieties of which I am aware, as evidenced by the following unique combination of characteristics which are outstanding therein:

(1) An exceptionally well-clothed plant habit particularly suited for use for hedge plantings;

(2) Attractive dark green foliage of medium size;

(3) Abundant blooms of medium size and double form;

(4) A habit of bearing the blooms in clusters or sprays; and (5) A distinctive and attractive flower color corresponding to Rose Madder on opening but intensifying to Crimson on exposure to sunlight as the flowers mature.

Asexual reproduction of my new variety by budding, as perforated at both Saugus and Shafter, California, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with the Horticultural Colour Chart of the British Colour Council, except where general color terms of ordinary dictionary significance are obvious:

Type: Half-hardy; tall; shrub; outdoor; seedling; for cut flowers and for garden decoration.
Class: Floribunda.
Breeding: Seedling.
*Seed parent.*—"Easter Parade."
*Pollen parent.*—"Herrenhausen."
Propagation: Holds its distinguishing characteristics through succeeding propagations by budding.

*Flower*

Locality where grown and observed: Shafter, California.
Flowers borne: Both singly and from 3 to 5 flowers to stem; in irregular rounded clusters; on short stems of normal strength.
Quantity of bloom: Abundant, outdoors.
Continuity: Continuous.
Fragrance: Moderate. Nature—spicy.
Bud:
*Peduncle.*—Short; medium heaviness; medium erectness; almost smooth; with few brown prickles. Color—Bronze.
*Before calyx breaks.*—Size—small. Form—pointed oval; without foliaceous appendages on the surface of the bud; with slender foliaceous parts extending beyond the tip of the bud equal to ¼ its length. Color—Veronese Green, Plate 660, page 89.

*As calyx breaks.*—Color—Oxblood Red, Plate 00823/3, page 191.
*As first petal opens.*—Size—small. Form—short; pointed ovoid. Color: Outside—Lemon Yellow, Plate 4/2, page 4; inside—Scarlet, Plate 19, page 19.
*Opening.*—Opens up well.
Bloom:
*Size (when fully open).*—Small; from 2½ inches to 3¼ inches.
*Petalage.*—Very double; from 45 to 55 petals; arranged regularly.
*Form.*—High-centered at first, but becoming open; petals being at first tightly rolled outward, but becoming loosely rolled outward at maturity.
Petals:
*Texture.*—Thick.
*Appearance.*—Inside—Satiny. Outside—Satiny.
*Shape.*—Outside—round; scolloped; with apex flat and with one notch. Intermediate—ovate. Inside—obovate.

This description of a newly opened flower was made from a rose grown outdoors during the month of June at Shafter, California:

*Color.*—Outer petal: Outside surface—Canary Yellow, Plate 2/3, page 2; inside surface—Rose Madder, Plate 23, page 23. Intermediate petal: Outside surface—Tangerine Orange, Plate 9/2, page 9; inside surface—Vermilion, Plate 18/1, page 18. Inner petal: Outside surface—Orange, Plate 12/2, page 12; inside surface—Scarlet, Plate 19/1, page 19.

This description was made from a rose that was open for three days outdoors during the month of June at Shafter, California:

*Color.*—Outer petal: Outside surface—Geranium Lake, Plate 20/3, page 20; inside surface—Crimson, Plate 22/1, page 22. Inner petal: Outside surface—Crimson, Plate 22/3, page 22; inside surface—Crimson, Plate 22/1, page 22.
*General color effect.*—Newly opened flower—Crimson, Plate 22/3, page 22. Three days open—Crimson, Plate 22/1, page 22.
*Behavior.*—Drop off cleanly; not noticeably affected by cold, hot wet or dry weather.
*Flower longevity.*—On bush in garden—5 days in June. Cut roses grown outdoors and kept at living-room temperatures—3 days in June.

*Reproductive organs*

Stamens: Medium number; arranged regularly; mixed with petaloids. Color—Indian Yellow, Plate 6/1, page 6.
Filaments: Medium length; most with anthers. Color—yellow.
Anthers: Small; open at various times. Color—yellow.
Pollen: Sparse. Color—lemon.
Pistils: Medium number.
Styles: Even; short; medium caliper; bunched.
Stigma: Color—yellow.
Ovaries: All enclosed in calyx
Hips: Ovoid; smooth; walls thick and fleshy. Color—reddish green.
Sepals: Permanent; moderate length; spear-shaped. Color—pea green, Plate 61/2, page 61.
Seeds: Few; medium size.

*Plant*

Foliage:

*Leaves.*—Compound of 5 leaflets; abundant; medium size; heavy; glossy.

*Leaflets.*—Shape—Ovoid. Apex—Acute. Base—round. Margin—simply serrate.

*Color.*—Mature: Upper surface—dark green; under surface—light green. Young: upper surface—very green bronze; under surface—very bronze.

*Rachis (the supporting stem of the compound leaf.*—Medium. Upper side smooth. Under side—moderately smooth.

*Stipules.*—Medium length; narrow; with points of medium length turning out at an angle of 45°.

*Disease resistance.*—Good resistance to mildew, as determined by comparison with other varieties grown under comparable conditions at Shafter, California.

Growth:

*Habit.*—Bushy; upright; much-branched.

*Growth.*—Vigorous.

*Canes.*—From medium to heavy caliper.

*Main stems.* — Color — green brown. Thorns—several; medium length; straight; with long, narrow base. Prickles—none. Hairs—none.

*Branches.*—Color—medium bright green. Thorns—few; medium length; straight; with narrow base. Prickles—many; color—reddish. Hairs—none.

*New shoots.*—Color—bright bronze. Thorns—several; medium length; straight; with narrow base. Prickles—none. Hairs—none.

I claim:

A new and distinct variety of rose plant of the floribunda class, substantially as herein shown and described, characterized particularly as to novelty by the unique combination of an exceptionally well-clothed plant habit particularly suited for use for hedge plantings, attractive dark green foliage of medium size, abundant blooms of medium size and double form, a habit of bearing the blooms in clusters or sprays, and a distinctive and attractive flower color corresponding to Rose Madder on opening but intensifying to Crimson on exposure to sunlight as the flowers mature.

No references cited.

ABRAHAM G. STONE, *Primary Examiner.*

R. E. BAGWILL, *Assistant Examiner.*